(12) United States Patent
Kuiper et al.

(10) Patent No.: US 11,324,944 B1
(45) Date of Patent: May 10, 2022

(54) FLEXIBLE CABLE ASSEMBLY FOR MEDICAL IMPLANTATION

(71) Applicant: Verily Life Sciences LLC, South San Francisco, CA (US)

(72) Inventors: Stein Kuiper, South San Francisco, CA (US); Kedar Shah, San Francisco, CA (US); Patricia Johnson, San Carlos, CA (US); Anil Ram Rakhyani, Union City, CA (US); Shungneng Lee, Sunnyvale, CA (US); Georges Geotz, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 162 days.

(21) Appl. No.: 16/520,123

(22) Filed: Jul. 23, 2019

(51) Int. Cl.
*A61N 1/05* (2006.01)
*A61N 1/08* (2006.01)
*H01B 7/08* (2006.01)
*H05K 1/02* (2006.01)
*A61N 1/375* (2006.01)

(52) U.S. Cl.
CPC ............. *A61N 1/05* (2013.01); *A61N 1/08* (2013.01); *A61N 1/3752* (2013.01); *H01B 7/0838* (2013.01); *H05K 1/0218* (2013.01)

(58) Field of Classification Search
CPC .......... A61N 1/05; A61N 1/08; A61N 1/3752; H01B 7/0838; H05K 1/0218
See application file for complete search history.

(56) References Cited

U.S. PATENT DOCUMENTS

| | | | |
|---|---|---|---|
| 3,612,743 A | 10/1971 | Angele et al. | |
| 3,612,744 A | 10/1971 | Thomas | |
| 5,359,496 A * | 10/1994 | Kornrumpf | ............. H01L 23/04 257/E21.505 |
| 5,736,430 A * | 4/1998 | Seefeldt | .............. B81C 1/00158 438/53 |
| 5,753,819 A * | 5/1998 | Rozgo | ................. G01L 19/0038 73/706 |
| 7,774,931 B2 * | 8/2010 | Tai | ........................ A61N 1/0543 29/832 |
| 8,095,224 B2 | 1/2012 | Truex et al. | |
| 8,195,295 B2 | 6/2012 | Stevenson et al. | |
| 9,205,253 B2 | 12/2015 | Olsen et al. | |
| 9,216,286 B2 | 12/2015 | Stone et al. | |
| 9,463,610 B2 * | 10/2016 | Tsotsis | .................... B32B 27/28 |

(Continued)

*Primary Examiner* — Timothy J Thompson
*Assistant Examiner* — Rhadames Alonzo Miller
(74) *Attorney, Agent, or Firm* — Christensen O'Connor Johnson Kindness PLLC (57) ABSTRACT

An electrical cable assembly amenable to implantation into a body includes a flexible cable. The flexible cable includes a dielectric substrate, a conductor lead for conducting an electrical signal, a conductive barrier layer, and an overmold layer. The conductor lead is embedded within and surrounded by the dielectric substrate. The conductive barrier layer surrounds the dielectric substrate and encases the dielectric substrate and conductor lead in a cavity. The conductive barrier layer is a continuous material layer that is neither braided nor spiral wrapped and provides a hermetic barrier formed of a metallic or inorganic material. The overmold layer provides one or more of mechanical protection or strain relief to the conductive barrier layer.

23 Claims, 5 Drawing Sheets

(56) References Cited

U.S. PATENT DOCUMENTS

| | | | |
|---|---|---|---|
| 2003/0122246 A1* | 7/2003 | Lin | H01L 23/5389 257/723 |
| 2004/0057978 A1* | 3/2004 | Mattes | A61L 27/34 424/423 |
| 2004/0127968 A1* | 7/2004 | Kuzma | A61N 1/0541 607/137 |
| 2004/0220651 A1* | 11/2004 | Kuzma | A61N 1/0541 607/137 |
| 2004/0267107 A1* | 12/2004 | Lessar | A61N 1/056 600/395 |
| 2005/0051243 A1* | 3/2005 | Forbes Jones | A61L 31/022 148/442 |
| 2005/0060885 A1* | 3/2005 | Johnson | A61B 18/1492 29/846 |
| 2005/0065508 A1* | 3/2005 | Johnson | A61N 1/05 606/41 |
| 2005/0065586 A1* | 3/2005 | Johnson | A61N 1/05 607/122 |
| 2006/0127439 A1* | 6/2006 | Mattes | A61L 29/10 424/422 |
| 2006/0265039 A1* | 11/2006 | Bartic | A61N 1/0534 607/116 |
| 2007/0151348 A1* | 7/2007 | Zdeblick | A61N 1/36564 73/708 |
| 2007/0160748 A1* | 7/2007 | Schugt | A61B 5/0215 427/117 |
| 2008/0046080 A1* | 2/2008 | Vanden Bulcke | H01L 23/3107 623/10 |
| 2009/0013791 A1* | 1/2009 | Zdeblick | A61B 5/0215 73/700 |
| 2009/0033863 A1* | 2/2009 | Blum | G02C 7/16 351/159.34 |
| 2009/0234368 A1* | 9/2009 | Gore | A61N 1/05 606/129 |
| 2009/0270958 A1* | 10/2009 | Greenberg | A61N 1/0543 607/116 |
| 2009/0276004 A1* | 11/2009 | Kronich | A61N 1/37211 607/36 |
| 2010/0036211 A1* | 2/2010 | La Rue | A61B 5/0002 600/301 |
| 2010/0075168 A1* | 3/2010 | Schaffer | C22C 19/055 428/544 |
| 2010/0148345 A1* | 6/2010 | Eckhardt | H01L 21/76898 257/690 |
| 2010/0206612 A1* | 8/2010 | Schiefer | A61N 1/05 174/119 R |
| 2010/0292760 A1* | 11/2010 | Leigh | A61N 1/375 607/57 |
| 2010/0314149 A1* | 12/2010 | Gerrish | H01L 24/05 174/50.52 |
| 2010/0324614 A1* | 12/2010 | Mattes | A61N 1/37512 607/6 |
| 2011/0004207 A1* | 1/2011 | Wallace | A61B 17/1757 606/35 |
| 2011/0270341 A1* | 11/2011 | Ruben | H01L 24/11 607/9 |
| 2012/0029343 A1* | 2/2012 | Wasson | H01F 41/041 600/424 |
| 2012/0112347 A1* | 5/2012 | Eckhardt | H01L 24/82 257/751 |
| 2012/0191003 A1* | 7/2012 | Garabedian | A61N 1/0551 600/554 |
| 2012/0197155 A1* | 8/2012 | Mattes | G01L 9/12 600/561 |
| 2013/0006118 A1* | 1/2013 | Pan | H01L 51/5024 600/476 |
| 2013/0006119 A1* | 1/2013 | Pan | H01L 51/5287 600/476 |
| 2013/0253344 A1* | 9/2013 | Griswold | A61N 1/0587 600/486 |
| 2013/0303020 A1* | 11/2013 | Sabin | A61N 1/3787 439/527 |
| 2013/0345780 A1* | 12/2013 | Tabada | A61N 1/0529 607/115 |
| 2014/0018884 A1* | 1/2014 | Leven | A61N 1/0558 607/72 |
| 2014/0163646 A1* | 6/2014 | Tischendorf | A61N 1/3756 607/60 |
| 2014/0318689 A1* | 10/2014 | Tsotsis | B32B 27/283 156/150 |
| 2015/0036302 A1* | 2/2015 | Tai | H01L 23/3135 361/752 |
| 2015/0142090 A1* | 5/2015 | Duijsens | A61N 1/05 607/116 |
| 2015/0157862 A1* | 6/2015 | Greenberg | H05K 1/11 607/60 |
| 2016/0066789 A1* | 3/2016 | Rogers | A61N 1/05 604/20 |
| 2017/0027514 A1* | 2/2017 | Biederman | A61B 5/1451 |
| 2017/0165051 A1* | 6/2017 | Mattes | B29D 11/00826 |
| 2017/0172731 A1* | 6/2017 | Mattes | A61F 2/1624 |
| 2017/0238991 A1* | 8/2017 | Worrell | H05K 3/061 |
| 2018/0078754 A1* | 3/2018 | Perez | A61B 5/4836 |
| 2018/0085580 A1* | 3/2018 | Perez | G09B 19/0092 |
| 2018/0333571 A1* | 11/2018 | Pepin | H01B 3/307 |
| 2019/0069949 A1* | 3/2019 | Vrba | A61B 18/02 |
| 2019/0104936 A1* | 4/2019 | Gunn | A61B 3/0025 |
| 2019/0142575 A1* | 5/2019 | Kuiper | A61F 2/1648 623/6.11 |
| 2019/0374213 A1* | 12/2019 | Goldsmith | A61F 2/042 |
| 2020/0215335 A1* | 7/2020 | McLaughlin | A61N 1/0553 |

* cited by examiner

FLEXIBLE CABLE ASSEMBLY FOR MEDICAL IMPLANTATION

TECHNICAL FIELD

This disclosure relates generally to medical implants, and in particular but not exclusively, relates to electrical cables for medical implants.

BACKGROUND INFORMATION

Electrically powered body implantable devices should include protection against ingress of body fluids as these body fluids can corrode circuit elements and cause electrolysis. Ingress and electrochemical corrosion occur especially in areas where electric fields are present because these fields cause electromigration of charged and polar molecules such as ions and water.

One conventional technique to reduce electric field induced ingress is to alternate the polarity on the charge carriers, so that the time-averaged field is zero. However, it is not always possible to use alternating voltages. For example, a battery will always have a positive and a negative contact. The constant direction of the electric field near these contacts makes it difficult to prevent ingress.

Rigid hermetically-sealed packages are commonly used to protect in-vivo electronics, but these may be difficult to employ in foldable devices such as variable-focus intraocular lenses and flexible microelectronic assemblies. Moreover, rigid hermetically-sealed packages are often too large or consume too much valuable space in certain volume constrained implantable devices. Barrier coatings applied directly over the electronics are also used, but these coatings are vulnerable when subjected to fixed-polarity electric fields due to time-dependent ingress. Moreover, folding of barrier coatings without damaging them is challenging.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of use for an electrical cable assembly amenable to implantation into a body are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of the present disclosure organize the charge carriers within a body implantable electrical cable assembly in such a way that the electric field experienced by body fluids surrounding the electrical cable assembly is significantly reduced, or eliminated, thereby improving device reliability and reducing tissue exposure. Similar to using alternating current (AC) for time-averaging an electric field to zero, a field can be spatially averaged to zero. This can be achieved by arranging the charge carriers in certain symmetric ways, similar to a coaxial layout. Embodiments disclosed herein use a conductive barrier layer that surrounds and encases one or more interior conductor leads. This conductive barrier layer enables charge carriers to organize and oppose electrostatic fields emanating from the conductor leads in a manner that is similar to a linear capacitor. In other words, the conductive barrier layer forms a conductive enclosure such that the electric field inside the enclosure or cavity does not penetrate outside, thus creating a reduced field in the tissue outside the implant. Within the electrical cable assembly, charges induced by the active circuitry or charged conductive leads are rearranged spatially to create a flatter electric field and avoid the creation of voltage biased 'hot-spots' at high voltage circuit nodes. Additionally, an insulating overmold layer is coating over the continuous material layer of the conductive barrier layer to provide mechanical protection, strain relief, and protection from passive ingress to further protect the adjacent tissue and body fluids.

In some embodiments, the electrical cable assembly may be used as an umbilical cord connecting an integrated circuit to another circuit component. In the case of an ophthalmic implant (e.g., accommodating intraocular lens), the active lens may be implanted into the capsular sack region of the eye while supporting electronics are remotely placed in peripheral regions of the eye, such as in the sclera. In this application, the active lens may include an integrated circuit that is electrically coupled to a battery, transceiver electronics, sensors, or otherwise representing the other circuit components. Where the active lens is implemented with an electrowetting-based optic, voltages typically up to 20V may be used to drive the active lens. As such, the electrical cable assembly (umbilical cord) should provide sufficient electrical shielding to prevent time-dependent ingress due to electric fields spilling out from the cable. Additionally, it is advantageous if the electrical cable assembly is flexible to enable folded insertion options to reduce incision sizes.

Figure 1:
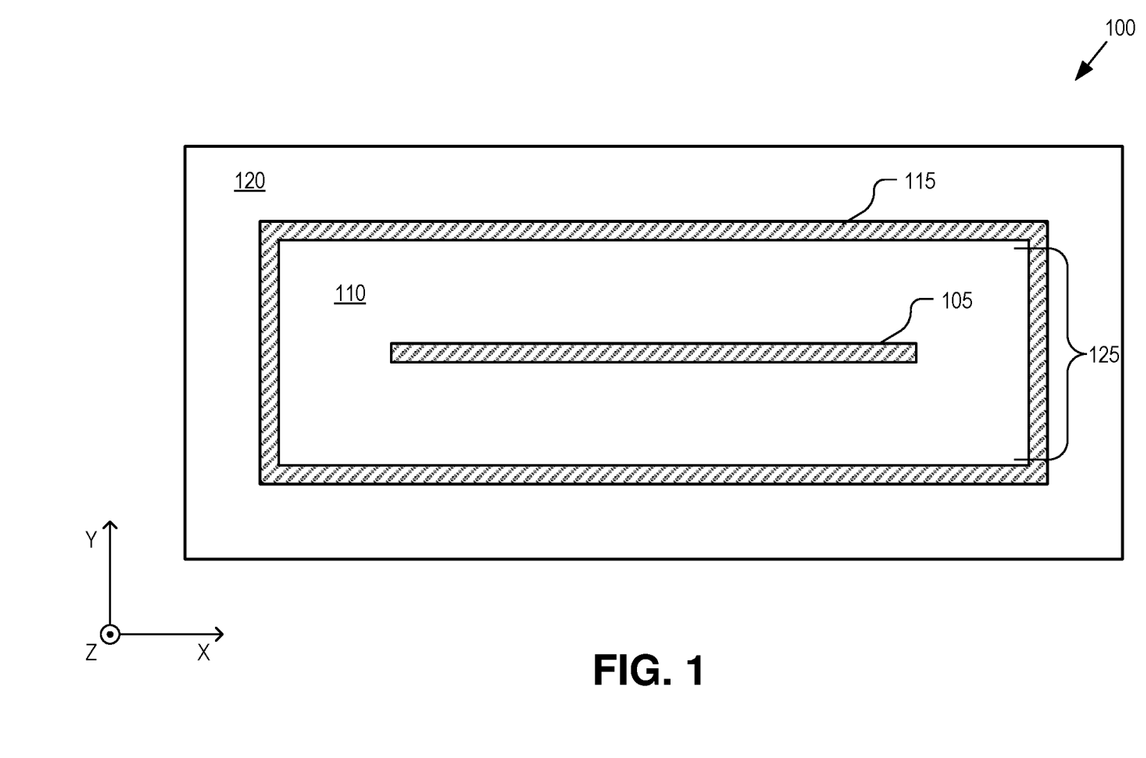
FIG. 1 is a cross-sectional end-view illustration of a flexible cable amenable to implantation into a body, in accordance with an embodiment of the disclosure.

FIG. 1 is a cross-sectional end-view illustration of a flexible cable 100 suitable for implantation into a body, in accordance with an embodiment of the disclosure. The illustrated embodiment of flexible cable 100 includes at least one conductor lead 105, a dielectric substrate 110, a conductive barrier layer 115, and an overmold layer 120.

Conductive barrier layer 115 surrounds and encases dielectric substrate 110 within an enclosure or cavity 125 defined by conductive barrier layer 115. In the illustrated embodiment, cavity 125 defined by conductive barrier layer 115 has a rectangular cross-sectional shape. Conductive lead 105 is a thin material layer (e.g., 2 um thick) disposed in the central area of cavity 125 referred to as a neutral stress plane when flexible cable 100 is folded or bent. The rectangular shape of flexible cable 100 results in a thinner overall cable (in at least one dimension) and thus is easier to bend relative to other form factors. In contrast, conventional coaxial cables are round making them difficult to fabricate thin enough to be foldable over a radius of 0.5 mm that is desirable for surgical implantation of intraocular lenses into an eye. For example, a coaxial cable having a titanium shield layer would need a 4 um diameter, or less, to achieve a 0.5 mm bend radius for eye implantation. Fabrication of such a small coaxial cable is exceedingly challenging.

Coax cables are usually made flexible by making the outer lead (shielding layer) out of braided or spiral wrapped cladding. However, for in-body use the non-continuous nature of braiding or spiral wrapped cladding would not prevent water from penetrating the space between the shielding and core conductors. Bending of conventional coaxial cables is possible due to sliding of the braided or spiral wrapped layers. The use of a uninterrupted foil cladding on a coaxial cable results in an inflexible cable. Accordingly, conventional coaxial cables are not suitable for implantation into a body and the relative inflexibility of a solid cladding in coaxial cables having a round cross-sectional shape is not suitable for implantation into compact spaces such as an eye. In contrast, the rectangular cross-sectional shape of cavity 125 and conductive barrier layer 115 is a configuration that lends itself well to tight radius bending for implantation of flexible cable 100 into an eye.

Conductive barrier layer 115 is a continuous material layer that provides a hermetic barrier. Conductive barrier layer 115 is formed of a metallic or inorganic material, such as gold, platinum, titanium, nickel titanium (Nitinol), or otherwise. As illustrated, conductive lead 105 is embedded within and surrounded by dielectric substrate 110. In one embodiment, dielectric substrate 110 is a multi-layer sandwich (e.g., each sandwich layer is 1 um thick) that encompasses one or more conductive leads 105. In the configuration illustrated in FIG. 1, dielectric substrate 110 may be about 2 um in total thickness. Dielectric substrate 110 may be fabricated from various insulating materials such as Parylene, Polyimide, or otherwise. The continuous material of conductive barrier layer 115 may be fabricated of a metal film (e.g., 100 nm thick) that is sputtered onto dielectric substrate 110, deposited using atomic layer deposition (ALD), or otherwise. To be effective as a hermetic barrier, conductive barrier layer 115 should be fabricated of metal or a conductive inorganic material.

Overmold layer 120 is a protective coating molded over conductive barrier layer 115. Overmold layer 120 may be fabricated of a silicone material, an elastomeric material, or otherwise. In some embodiments, overmold layer 120 is a multi-layer coating that operates as both a moisture barrier (in addition to conductive barrier layer 115) and a mechanical strain relief. In various applications, overmold layer 120 may range between 10 um to 100 um thick depending upon the desired mechanical properties and strain relief.

The rectangular cross-sectional geometry of cavity 125 not only facilitates tight bending radiuses (e.g., 0.5 mm) without exceeding the yield strain of conductive barrier layer 115, but also serves to reduce electric field leakage from cavity 125. For example, conductive barrier layer 115 may be electrically grounded and operate as a ground plane that surrounds conductor lead 105. This configuration of conductive barrier layer 115, dielectric substrate 110, and conductor lead 105 forms a linear capacitor that contains static electric fields within cavity 125. The entire linear capacitor stack has a neutral charge, and for a DC signal little or no electric field will leak outside of cavity 125. Accordingly, ions and water from surrounding tissue are not significantly attracted towards flexible cable 100. In yet another embodiment, conductive lead 105 may be coupled as the positive polarity lead (or time-averaged positive polarity lead) and fabricated of a valve metal (e.g., Al, Hf, Hb, Ta, Ti, Zr, W, V, or Be), or valve alloy, so that anodization due to intrusion stops current from flowing. The valve metal provides additional protection in the event of an accidental ingress through damage in overmold layer 120 and conductive barrier layer 115.

The thickness of flexible cable 100 can be increased, and thus made more robust, if conductive barrier layer 115 is made of more elastic materials such as superelastic nitinol, relative to gold or titanium. Nitinol can stretch elastically up to 8% (compare to only 0.4% for titanium). The maximum thickness of a plate that can elastically bend is given by $$t_y = 2r\varepsilon_y$$

where $t_y$ is the thickness at which the plate yields, $r$ is the bend radius, and $\varepsilon_y$ is the yield strain. With a yield strain of 0.08 and a bending radius of 0.5 mm, flexible cable 100 can be 80 µm thick, provided that overmold layer 120 has a yield strain much larger than 0.08. Flexible cable 100 is preferably positioned in the neutral tension plane of a device, so that the stress during bending is minimal.

Figure 2:
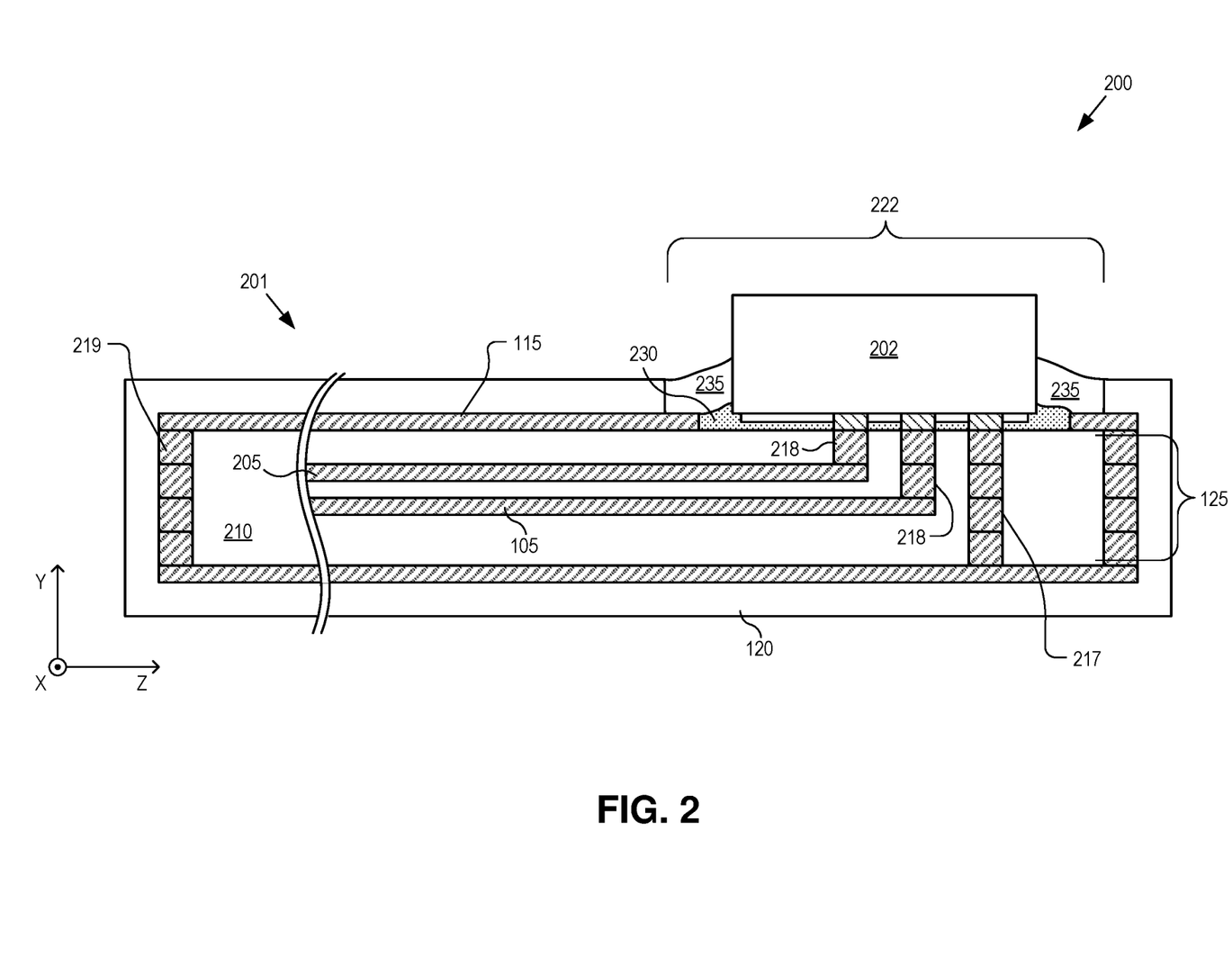
FIG. 2 is a cross-sectional side-view illustration of a flexible cable assembly including a flexible cable attached to an integrated circuit, in accordance with an embodiment of the disclosure.

FIG. 2 is a cross-sectional side-view illustration of a flexible cable assembly 200 including a flexible cable 201 attached to an integrated circuit 202, in accordance with an embodiment of the disclosure.

Flexible cable 201 is similar to flexible cable 100, but includes additional features. For example, the flexible cable 201 includes multiple conductor leads 105 and 205 embedded within a three layer dielectric substrate 210. In the illustrated embodiment, conductor leads 105 and 205 run parallel to each other within the shielded cavity 125 provided by conductive barrier layer 115. During operation, conductor leads 105 and 205 may be differential leads and thus spatially average to a net zero potential. Flexible cable 201 also includes interior ground via 217 disposed within cavity 125 and extending across cavity 125 in an interior region of cavity 125 to short circuit opposite sides of conductive barrier layer 115. This maintains a more uniform ground potential across interior regions of flexible cable 201. In one embodiment, ground vias 217 are fabricated of metal layers. In the illustrated embodiment, ground vias 217 is also connected to a ground contact on integrated circuit 202 to tie the ground of integrated circuit 202 to conductive barrier layer 115. Yet another feature of flexible cable 201 is the use of edge vias 219 to build up the end caps of conductive barrier layer 115. Of course, the end caps may alternatively be fabricated using the same sputtering or ALD processes used to fabricate the other portions of conductive barrier layer 115.

In FIG. 2, integrated circuit 202 is connected to an end region of flexible cable 201, which includes a mounting region 222 where overmold layer 120 and conductive barrier layer 115 are absent (e.g., removed). The exposed portion of mounting region 222 enables integrated circuit 202 to be bonded to flexible cable 201. Electrical connections are formed between contacts on the underside of integrated circuit 202 and conductive leads 105, 205 with signal vias 218. The mechanical bond may be formed using an insulating epoxy adhesive 230. In one embodiment, the insulating epoxy adhesive 230 is a cured anisotropic conductive paste (ACP) or a non-conductive paste (NCP). The electrical contacts of integrated circuit 202 coupled to vias 217 or 218 may be bonded via thermo-compressive bonding (TCB). For example, gold solder bumps may be used.

Mounting region 220 is electrically and hermetically sealed by application of a conductive conforming material 235 disposed over the perimeter gaps in mounting region 222 extending around integrated circuit 202. Conductive conforming material 235 connects sides of integrated circuit 202 to exposed portions of conductive barrier layer 115. In one embodiment, conductive conforming material 235 is a conductive paste, such as a silver alcohol suspension, an ALD metal, or otherwise. In the illustrated embodiment, integrated circuit 202 is formed from a bare silicon die without an encasing package. The conductive nature of doped bulk silicon provides a conductive barrier that inherently prevents leakage of electromagnetic radiation when its side surface or bulk is otherwise grounded. As such, conductive conforming material 235 serves to electrically short the silicon bulk to conductive barrier layer 115. The conductive conforming material 235 along with the silicon bulk become part of the ground plane enclosing conductive leads 105 and 205.

Figure 3:
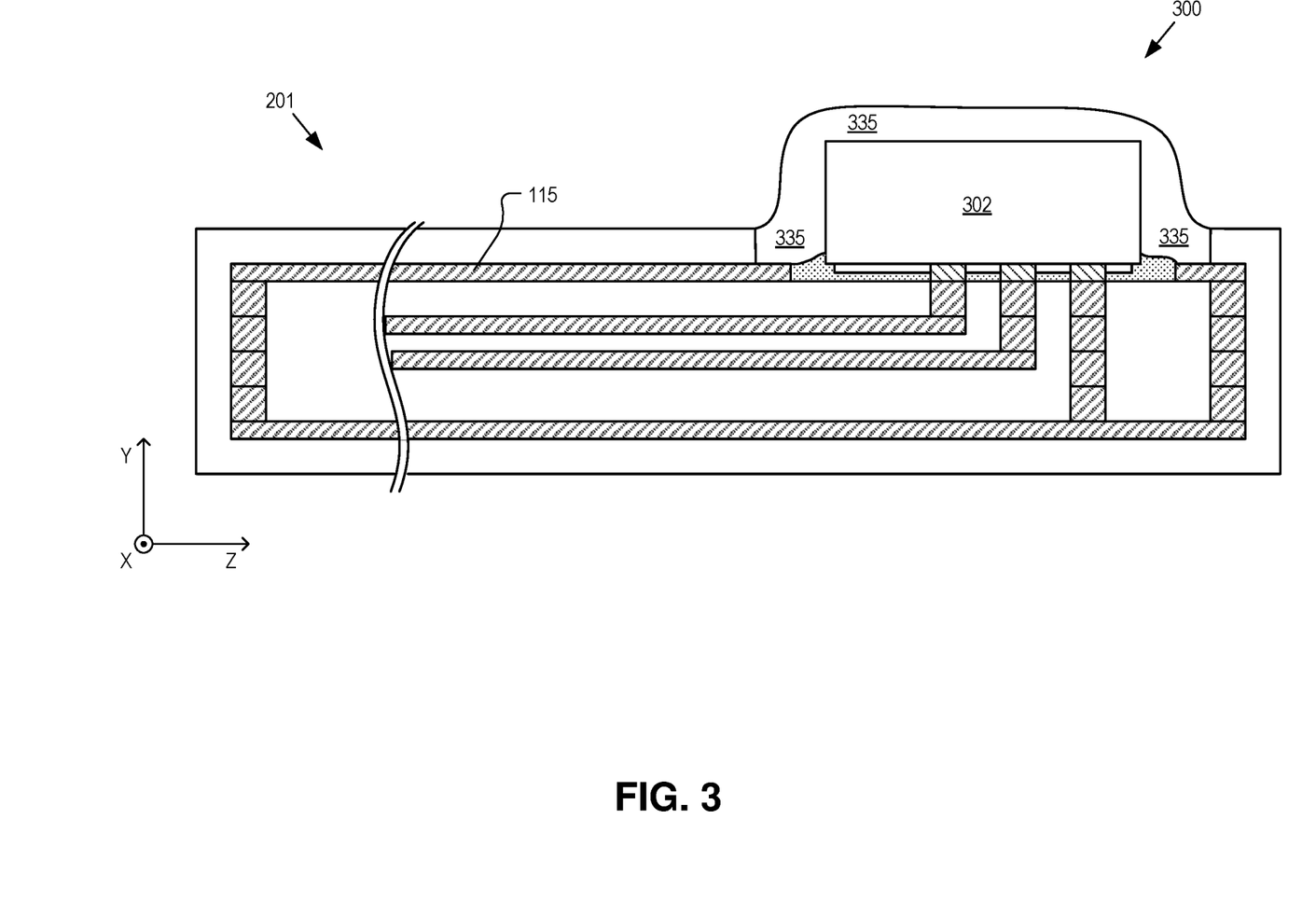
FIG. 3 is a cross-sectional side-view illustration of a flexible cable assembly including a flexible cable attached to an integrated circuit, in accordance with an embodiment of the disclosure.

FIG. 3 is a cross-sectional side-view illustration of a flexible cable assembly 300 including a flexible cable 201 attached to an integrated circuit 302, in accordance with an embodiment of the disclosure. Flexible cable assembly 300 is similar to flexible cable assembly 200 except that conductive conforming material 335 is coated over the entirety of integrated circuit 302, as opposed to just covering the perimeter gaps around the integrated circuit. Conductive conforming material 335 may be coated entirely over integrated circuit 302 to improve electrical and/or environmental isolation, or may be used in scenarios where integrated circuit 302 is not a bare silicon die. For example, integrated circuit 302 may be a silicon-on-insulator (SOI) system, fabricated on sapphire or glass, or packaged in other non-conductive materials. These non-conductive structures may not provide the necessary conductive surfaces to electrically short to the ground plane provided by conductive barrier layer 115.

Figure 4:
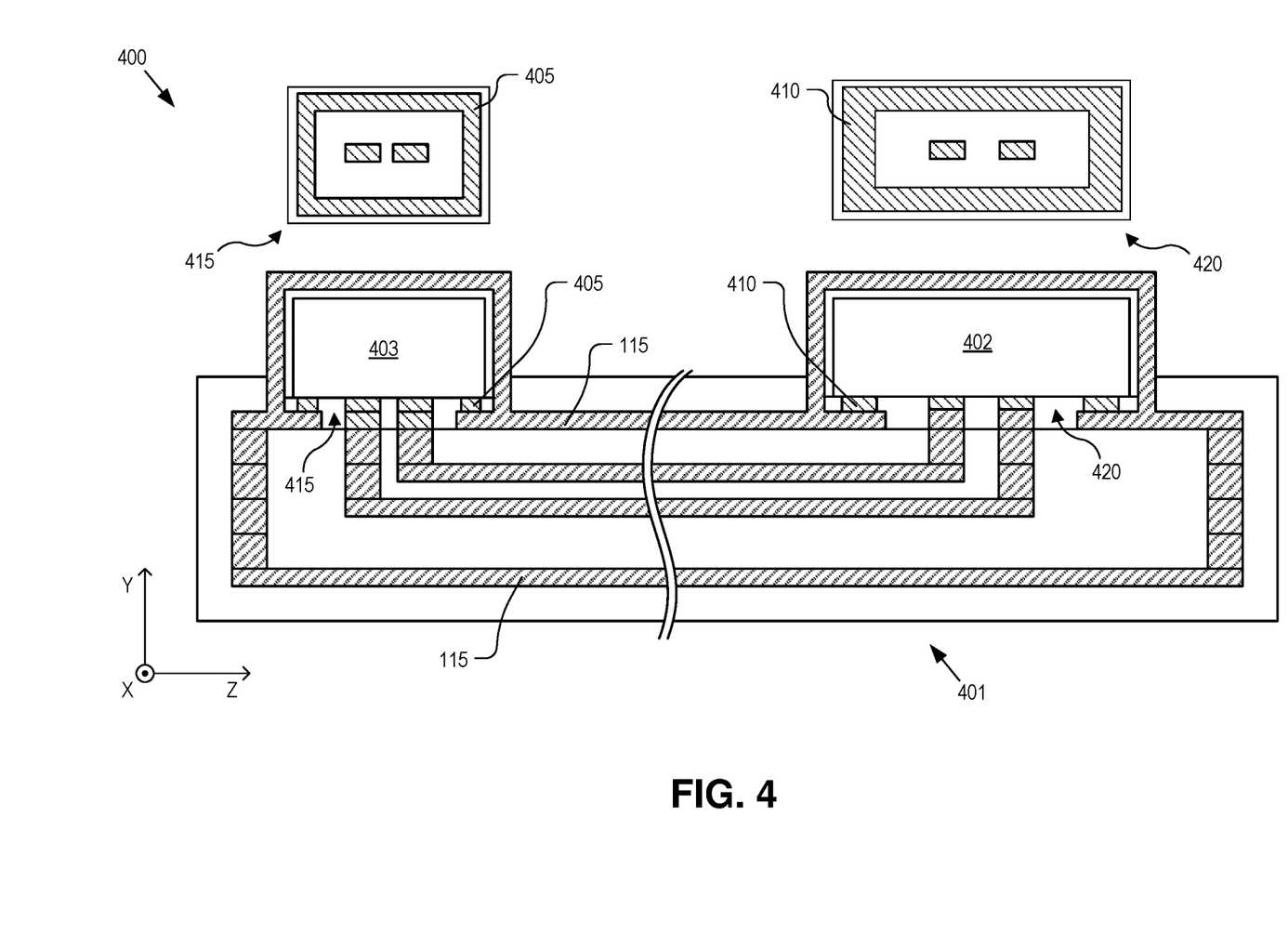
FIG. 4 is a cross-sectional side-view illustration of a flexible cable assembly including a flexible cable operating as an umbilical cord between an integrated circuit and a circuit component, in accordance with an embodiment of the disclosure.

FIG. 4 is a cross-sectional side-view illustration of a flexible cable assembly 400 including a flexible cable 401 operating as an umbilical cord between an integrated circuit 402 and a circuit component 403, in accordance with an embodiment of the disclosure.

Circuit component 403 may include a variety of components that power or otherwise communicate with integrated circuit 402. In the example where flexible cable 401 interconnects components of an accommodating intraocular lens, integrated circuit 402 may be included with a variable power accommodating lens (e.g., electrowetting lens) that is implanted into the capsular sack, while circuit component 403 may include supporting electronics that are implanted into the sclera. For example, circuit component 403 may include a communication transceiver (e.g., RFID tag), a battery, one or more sensors, or otherwise. The battery may power integrated circuit 402 and the accommodating lens over flexible cable 401 while the transceiver circuitry may facilitate off-device communications with an external reader. The EM shielded nature of flexible cable 401 enables the relaying of higher supply voltages (e.g., 20V) to an electrowetting lens without flexible cable 401 being susceptible to time-dependent ingress. The flexible nature of flexible cable 401 facilitates a folded insertion into the eye using a minimally invasive, smaller incision.

The illustrated embodiment of flexible cable assembly 400 includes sealing rings 405 and 410. Sealing ring 405 electrically connects and physically seals the underside 415 of circuit component 403 to conductive barrier layer 115 of flexible cable 401. Sealing ring 410 electrically connects and physically seals the underside 420 of integrated circuit 402 to conductive barrier layer 115 of flexible cable 401. Sealing rings 405 and 410 may be formed of a metallic material that bonds via TCB, ultrasonic bonding, or otherwise.

Figure 5:
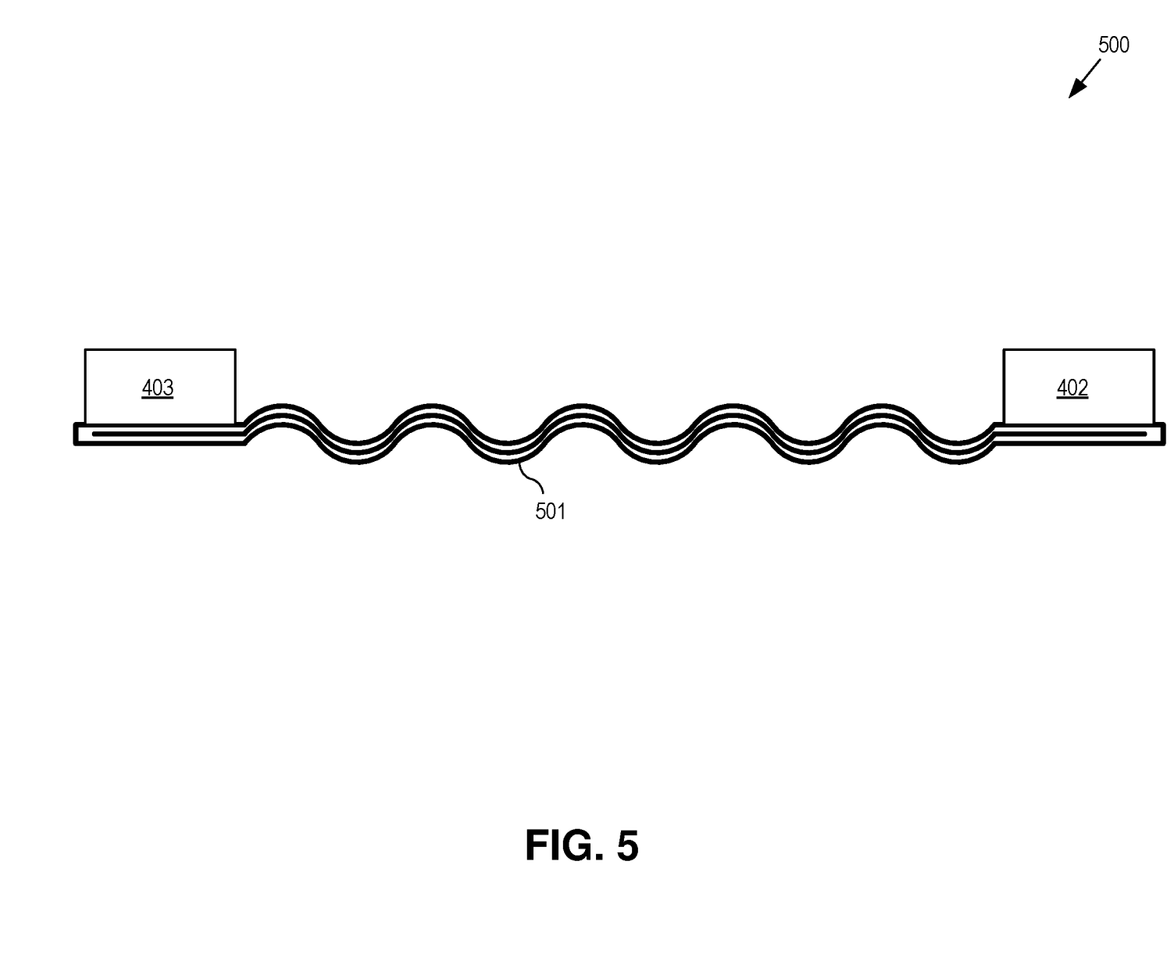
FIG. 5 illustrates the flexible cable having an undulating wave pattern along its length, in accordance with an embodiment of the disclosure.

FIG. 5 illustrates the flexible cable assembly 500 including a flexible cable 501 having an undulating wave pattern along its length, in accordance with an embodiment of the disclosure. Flexible cable 501 is molded into the undulating wave shape to increase its flexibility and reduce stresses when bending. Any of the flexible cables described above may be molded into the undulating wave pattern during manufacture, if desired.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:
1. An electrical cable assembly suitable for implantation into a body, the electrical cable assembly comprising:
   a flexible cable including:
      a dielectric substrate;
      a conductor lead for conducting an electrical signal, the conductor lead embedded within and surrounded by the dielectric substrate;
      a conductive barrier layer surrounding the dielectric substrate and encasing the dielectric substrate and conductor lead in a cavity, the conductive barrier layer being a continuous material layer that is neither braided nor spiral wrapped and provides a hermetic barrier formed of a metallic or conductive inorganic material;
      an overmold layer to provide one or more of mechanical protection or strain relief to the conductive barrier layer; and
      one or more grounding vias disposed within the cavity and extending across the cavity in an interior region of the cavity to short circuit opposite sides of the conductive barrier layer at the interior region.

2. The electrical cable assembly of claim 1, wherein the dielectric substrate comprises two layers of either Parylene or Polyimide that sandwich the conductor lead therebetween and wherein the continuous material layer of the conductive barrier layer comprises a sputtered metal film or an atomic layer deposited metal film.

3. The electrical cable assembly of claim 1, wherein the flexible cable and the cavity defined by the conductive barrier layer have a rectangular cross-section.

4. The electrical cable assembly of claim 3, wherein the flexible cable is molded into an undulating wave shape.

5. The electrical cable assembly of claim 3, wherein the conductive barrier layer, the dielectric substrate, and the conductor lead form a linear capacitor that contains a direct current (DC) electric field emitted by the electrical signal to within the cavity when the electrical signal is flowing through the conductor lead.

6. The electrical cable assembly of claim 5, wherein the conductive barrier layer comprises a ground plane surrounding the conductor lead.

7. The electrical cable assembly of claim 6, wherein the conductive barrier layer comprises a hermetic moisture barrier that hermetically seals the conductor lead within the cavity.

8. The electrical cable assembly of claim 1, wherein the overmold layer comprises a multi-layer coating that is both a moisture barrier and a mechanical strain relief.

9. The electrical cable assembly of claim 1, wherein the flexible cable further includes:
a plurality of conductor leads, including the conductor lead, embedded within the dielectric substrate and extending parallel to each other within the cavity, wherein the conductor leads are disposed on different planes within the cavity.

10. The electrical cable assembly of claim 9, further comprising
an integrated circuit mounted to first end region of the flexible cable, wherein a first contact on the integrated circuit is electrical coupled to one of the plurality of conductor leads using a first signal vias.

11. The electrical cable assembly of claim 10, further comprising:
a circuit component coupled to the second end region of the flexible cable opposite the first end region, wherein a second contact on the circuit component is electrically coupled to the one of the plurality of conductor leads using a second signal vias, wherein the flexible cable operates as an umbilical cord between the integrated circuit and the circuit component.

12. The electrical cable assembly of claim 10, wherein the first end region of the flexible cable includes an mounting region where the overmold layer and the conductive barrier layer are absent, wherein the integrated circuit is bonded to the mounting region, and wherein a conductive conforming material is disposed over perimeter gaps in the mounting region extending around the integrated circuit and electrically connects sides of the integrated circuit to exposed portions of the conductive barrier layer encircling the mounting region.

13. The electrical cable assembly of claim 12, wherein the integrated circuit comprises a bare silicon die without an encasing package.

14. The electrical cable assembly of claim 12, wherein the conductive conforming material is coated over an entirety of the integrated circuit.

15. The electrical cable assembly of claim 10, further comprising:
a seal ring formed of a conductive material extending around a perimeter of an underside of the integrated circuit that mates to the flexible cable, wherein the seal ring electrically connects and physically seals the underside of the integrated circuit to the conductive barrier layer.

16. A flexible umbilical cord amenable to implantation into a body and configurable for connecting an electrical component to an integrated circuit, the flexible umbilical cord comprising:
a dielectric substrate;
a conductor lead for conducting an electrical signal, the conductor lead embedded within and surrounded by the dielectric substrate;
a conductive barrier layer surrounding the dielectric substrate and encasing the dielectric substrate and conductor lead in a cavity, the conductive barrier layer being a continuous material layer that is neither braided nor spiral wrapped and provides a hermetic barrier formed of a metallic or inorganic material, wherein the cavity defined by the conductive barrier layer has a rectangular cross-section; and
one or more grounding vias disposed within the cavity and extending across the cavity in an interior region of the cavity to short circuit opposite sides of the conductive barrier layer at the interior region.

17. The flexible umbilical cord of claim 16, further comprising:
an overmold layer coated over the conductive barrier layer to provide one or more of mechanical protection or strain relief to the conductive barrier layer.

18. The flexible umbilical cord of claim 17, wherein the conductive barrier layer, the dielectric substrate, and the conductor lead form a linear capacitor that contains a direct current (DC) electric field emitted by the electrical signal to within the cavity when the electrical signal is flowing through the conductor lead.

19. The flexible umbilical cord of claim 17, wherein the conductive barrier layer comprises a ground plane surrounding the conductor lead.

20. The flexible umbilical cord of claim 17, wherein the conductive barrier layer comprises a hermetic moisture barrier that hermetically seals the conductor lead within the cavity.

21. The flexible umbilical cord of claim 17, wherein the overmold layer comprises a multi-layer coating that is both a moisture barrier and a mechanical strain relief.

22. The flexible umbilical cord of claim 16, wherein the flexible cable further includes:
a plurality of conductor leads, including the conductor lead, embedded within the dielectric substrate and extending parallel to each other within the cavity, wherein the conductor leads are disposed on different planes within the cavity.

23. The flexible umbilical cord of claim 17, wherein the dielectric substrate, the conductor lead, the conductive barrier layer, and the overmold layer have a molded-in undulating wave shape along a length of the flexible umbilical cord.

* * * * *

UNITED STATES PATENT AND TRADEMARK OFFICE
CERTIFICATE OF CORRECTION

PATENT NO. : 11,324,944 B1
APPLICATION NO. : 16/520123
DATED : May 10, 2022
INVENTOR(S) : Kuiper et al.

Page 1 of 1

It is certified that error appears in the above-identified patent and that said Letters Patent is hereby corrected as shown below:

In the Claims

| Column | Line |  |
|---|---|---|
| 7 | 39 | change "to first" to -- to a first --. |
| 7 | 41 | change "electrical" to -- electrically --. |
| 8 | 63 | change "card" to -- cord --. |

Signed and Sealed this
Twenty-sixth Day of August, 2025

Coke Morgan Stewart
*Acting Director of the United States Patent and Trademark Office*